United States Patent
Yoshiba (12)

(10) Patent No.: US 6,429,307 B1
(45) Date of Patent: Aug. 6, 2002

(54) **PROMOTER FOR '-PYRROLINE-5-CARBOXYLATE SYNTHETASE GENE IN *ARABIDOPSIS THALIANA***

(75) Inventor: Yoshu Yoshiba, Ageo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/635,587

(22) Filed: Aug. 9, 2000

(30) Foreign Application Priority Data

Aug. 17, 1999 (JP) .......................................... 11-230287

(51) Int. Cl.[7] .......................... A01H 5/00; C07H 21/04; C12N 15/00; C12N 15/63; C12N 15/82
(52) U.S. Cl. .................. 536/24.1; 435/320.1; 435/419; 435/468; 800/278; 800/298
(58) Field of Search ...................... 536/24.1; 435/320.1, 435/419, 468; 800/278, 298

(56) References Cited

U.S. PATENT DOCUMENTS 5,639,950 A    6/1997   Verma et al.

OTHER PUBLICATIONS

Kaye et al, "characterization of a Gene for Spinach CAP160 and Expression of Two Spinach Cold–Acclimation Proteins in Tobacco", 1998, Plant Physiol vol. 116, pp. 1367–1377.*
Rounsley, S. D. et al., Accession AC003000, Nov. 26, 1997.*
Yoshiba, Y. et al., "Stress–Responsive and Developmental Regulation of . . . Gene Expression in Arabidopsis thaliana." 1999, Biochemical and Biophysical Res. Comm., vol. 261, pp. 766–772.*
Kim, Y. et al., "A 20 nucleotide upstream element is essential for the nopaline synthase (nos) promoter activity." 1994, Plant Molecular Biology, vol. 24, pp. 105–117.*
Benfey, P. N. and Chua N. "The Cauliflower Mosaic Virus 35S Promoter: Combinatorial Regulation of Transcription in Plants." 1990, Science, vol. 250, pp. 959–966.*

Zhang et al., Characterization of $\Delta^1$–pyrroline–5–carboxylate synthetase gene promoter in transgenic Arabidopsis thaliana subjected to water, Plant Science vol. 129, 1997, pp. 81–89, whole document, especially Results and Discussion, and figs 1, 3, 4.
Strizhov et al. Differential expression of two P5CS genes controlling proline accumulation during salt–stress requires ABA and is regulated by ABA1, ABI1 and AXR2 In Arabidopsis, The Plant Journal 1997, vol. 12(3), pp. 557–569, whole document, especially Results, Discussion and Figures.
Savoure et al. Isolation, characterization and Chromosomal location of a gene encoding the $\Delta^1$–pyrroline–5–carboxylate synthetase in Arabidopsis thaliana, FEBS Letters 1995, vol. 372, pp. 13–19, see whole document, especially discussion.
Yoshiba et al., "Correlation between the induction of a gene for $\Delta^1$–pyrroline–5–carboxylate synthetase and the accumulation in Arabidopsis thaliana under osmotic stress" (Plant J. 1995).
Yoshiba et al., "Regulation of levels of Proline as an Osmolyte in Plants under water stress" (Plant Cell Phys. 1997).
Jefferson et al., "GUS fusions: β–glucuronidase as a senstive and versatile gene fusion marker in higher plants" (EMBO J. 1989).
Bechtold et al., "CR Acad. Sci. Ser. III Scie. Vie." (1993).
Sambrook et al., "Molecular Cloning" (Cold Spring Harbor Lab. 1989).

* cited by examiner

*Primary Examiner*—Elizabeth F. McElwain
*Assistant Examiner*—Cynthia Collins

(57) ABSTRACT

A genomic DNA library of *A. thaliana*, Columbia ecotype is screened by a plaque hybridization using the full-length P5CS1 cDNA as a probe. Positive clons are purified. These clones are subcdoned and sequence thereof is determined by cycle sequencing methods. Then deletion series of DNA is combined to GUS gene and introduced to *A. thaliana*. Using the transgenic *A. thaliana* plants, an analysis of the activity of GUS gene is determined and the activity region of the P5CS1 promoter is checked. It becomes clear that the P5CS1 promoter of *A. thaliana* controls expression of gene under water stress.

8 Claims, 6 Drawing Sheets

FIG. 2

```
tttgcccag ttatgattta taaaccctac aatttagtat caaagttttt attaaaatt     -1201
ctgaatctga cattaatgat atctggctca tttacagagc caatgagatg gatgatgttc   -1141
gaaactggat tggccattat ttaccttttt tttatctgga gaatcctcga ttggcacaaa   -1081
                      ↓-1064
cattatcata ttagccttta gaaattggat tggctaatca cacatttata tatattctta   -1021
ccaaaataaa tcacctctcc cgtaattgaa aaatatctaa atactgtaag tctgaaaaaa   -961
ttcacaaggg tccgaagaaa gaaggaaata tctaagcatc attaataaac tatctgtaac   -901
ctgagggaaa atcatttcat gttgaaatat gtggatttgg aagttttata atctatctga   -841
atttgtgaaa tttgataaca agtaagattt gtttcttaac acaaatctaa aatttgtttt   -781
ctaattaggt ttgagagaga gagagaaaga aacgctttgt atgatacaca tctaggctat   -721
gaatgaaggc ccagcggaca aagcggtcta aatttgtctg cggttttagt cccaatcctc   -661
                                            ↓-621              CCAAT
attttctgg ggtggacaat aaaccgctgc ggaccaagtt tatttgtatg taaaaacggt    -601
```

FIG. 3

```
ccgcagatgg tccgaaacga ttttcttcta ttttttaag tccagaccac tgcggactat   -541
     MYC                              -504
aattgatgaa tgataaataa aaaacggtct gaaccgttga cggttttgtc cgccccaacc   -481
         -470                                                 MYB
gccataacca ttcaaacccc taattatttc atcagataac attatacact aataatcatt   -421
    MYB                                              -374
gcactcaaat atgtcacaca atcatataat aaaataataa caatgattaa aatgaaaaaa   -361
ttgttgtggc gccgcataaa atagaaatcg tgagagacga cgtcatctaa aaattgcctt   -301
gctgtccact tttcactttg tcctctcttc tcatctccgt tcacttccac ggcgtttcct   -241
                                   -263
cagccgccga ttttatttat ttcccaaaat accatcacc tatagcgcca caatcctcta   -181
catcacaccc taatctcatt accatacacc acccaacgaa cacgcgccac ttcatttgtt   -121
     -116                                                 MYC
agtatctaaa ataccaaacc taccccttagt tccacacgtg gcgtttcctg gtttgataac    -61
                                       ABRE            -69
agagcctgag tctctggtgt cgctggtgtt tataaacccc ttcatatctt ccttggtgat     -1
                                  TATA
ctccaccttt ccctcacctg atatttattt tcttaccttta aatacgacgg tgcttcactg     60
  +1
agtccgactc agttaactcg ttcctctctc tgtgtgtggt tttggtagac gacgacgacg    120
ata atg gag gag cta gat cgt tca cgt gct gct ttt gcc aga gac gtc aaa  168
    Met Glu Glu Leu Asp Arg Ser Arg Ala Ala Phe Ala Arg Asp Val Lys cgt atc gtc gtt aag gtt cgt gagatacgtt cgcatttca                    210
Arg Ile Val Val Lys Val
```

 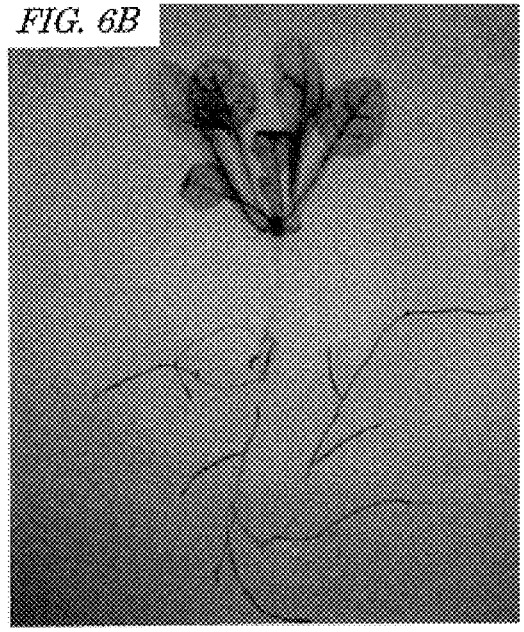

SEQUENCE LISTING

<160> NUMBER OF SEQ ID NOS: 1

<210> SEQ ID NO 1
<211> LENGTH: 1470
<212> TYPE: DNA
<213> ORGANISM: Arabidopsis thaliana
<220> FEATURE:
<221> NAME/KEY: promoter
<308> DATABASE ACCESSION NUMBER: AB022784
<309> DATABASE ENTRY DATE: 1999-01-28

<400> SEQUENCE: 1

```
ttttgcccag ttatgattta taaaccctac aatttagtat caaagttttt atttaaaatt      60
ctgaatctga cattaatgat atctggctca tttacagagc caatgagatg gatgatgttc     120
gaaactggat tggccattat ttacctttt tttatctgga gaatcctcga ttggcacaaa     180
cattatcata ttagccttta gaaattggat tggctaatca cacatttata tatattctta     240
ccaaaataaa tcacctctcc cgtaattgaa aaatatctaa atactgtaag tctgaaaaaa     300
ttcacaaggg tccgaagaaa gaaggaaata tctaagcatc attaataaac tatctgtaac     360
ctgagggaaa atcatttcat gttgaaatat gtggatttgg aagttttata atctatctga     420
atttgtgaaa tttgataaca agtaagattt gtttcttaac acaaatctaa aatttgtttt     480
ctaattaggt ttgagagaga gagagaaaga aacgctttgt atgatacaca tctaggctat     540
gaatgaaggc ccagcggaca aagcggtcta aatttgtctg cggttttagt cccaatcctc     600 attttctgg ggtggacaat aaaccgctgc ggaccaagtt tatttgtatg taaaaacggt     660
ccgcagatgg tccgaaacga ttttcttcta tttttttaag tccagaccac tgcggactat     720
aattgatgaa tgataaataa aaaacggtct gaaccgttga cggttttgtc cgccccaacc     780
gccataacca ttcaaacccc taattattc atcagataac attatacact aataatcatt     840
gcactcaaat atgtcacaca atcatataat aaaataataa caatgattaa aatgaaaaaa     900
ttgttgtggc gccgcataaa atagaaatcg tgagagacga cgtcatctaa aaattgcctt     960
gctgtccact tttcactttg tcctctcttc tcatctccgt tcacttccac ggcgtttcct    1020
cagccgccga ttttatttat ttcccaaaat acccatcacc tatagcgcca caatcctcta    1080
catcacaccc taatctcatt accatacacc acccaacgaa cacgcgccac ttcatttgtt    1140
agtatctaaa ataccaaacc tacccttagt tccacacgtg gcgtttcctg gtttgataac    1200
agagcctgag tctctggtgt cgctggtgtt tataaacccc ttcatatctt ccttggtgat    1260 ctccacctt ccctcacctg atatttattt tcttaccta aatacgacgg tgcttcactg    1320
agtccgactc agttaactcg ttcctctctc tgtgtgtggt tttggtagac gacgacgacg    1380
``` ata atg gag gag cta gat cgt tca cgt gct ttt gcc aga gac gtc aaa      1428
    Met Glu Glu Leu Asp Arg Ser Arg Ala Phe Ala Arg Asp Val Lys
     1               5                  10                  15 cgt atc gtc gtt aag gtt cgtt gagatacgtt cgcattttca                   1470
Arg Ile Val Val Lys Val
            20

PROMOTER FOR '-PYRROLINE-5-CARBOXYLATE SYNTHETASE GENE IN *ARABIDOPSIS THALIANA*

BACKGROUND OF THE INVENTION

The present invention relates to a promoter for a $\Delta^1$-pyrroline-5-carboxylate synthetase gene in *Arabidopsis thaliana* (referred as P5CS hereafter). Gene recombination is useful for the development of new plants or for the reproduction of culture cell so as to produce useful material.

It is known that many plants, including halophytes, accumulate compatible proline when they are exposed to osmotic stress. The fact suggests that the proline accumulated in plant organs plays a role in keeping water in the plant organs.

In plants, proline is produced from glutamic acid via both enzymes of P5CS and Δ1-pyrroline-5-carboxylate reductase (referred as P5CR hereafter). In a plant that has accumulated proline in its organs, when the activity of P5CS and the expression level of the P5CS gene increase as when they are exposed to water stress (dry stress or osmotic stress which means that plant has difficulty getting water), the activity of P5CR and the expression level of the P5CR gene do not change and remain at a low level. This suggests that the expression of P5CS controls a rate-limiting step of the production of the proline in plants under water stress (Yoshiba et al. Plant J. 7: 751–760 (1995)). Further, the expression of P5CS gene is induced not only under water stress such as dry stress or osmotic stress, but also by an abscisic acid (ABA)-dependent pathway. And the expression of the P5CS gene is suppressed in the absence of osmotic stress (Yoshiba et al. Plant Cell Physiol. 38:1095–1102 (1997)).

A conventional promoter based on a vector for plant is a promoter derived from a gene of a cauliflower mosaic virus (CaMV), or a promoter derived from a gene of a Ti plasmid of agrobacterium tumefacience (which is a kind of soil microorganism). These promoters are used as a promoter which effectively expresses a gene introduced into a plant.

SUMMARY OF THE INVENTION

The technology for introducing of gene into a plant is generally known. Further, a promoter which effectively expresses a gene introduced into the plant is also developed and used. The promoter based on a vector for the plant is used as an example. FIG. 1A shows that a promoter 101 is combined with a gene introduced into a plant so that a gene expression is induced by the promoter.

However, these conventional promoters express the respective gene after it is introduced into a plant regardless of a growing period or any part of the plant. A plant's growing usually does not require such a gene expression, and a gene expression is not good, in many cases, for a plant's growing. So if it is possible to control gene expression according to a desired condition, it is very useful for a plant's growing. Namely, if it is possible to realize a promoter specified to a growing period, a promoter specified to a tissue of plant or a promoter specified to an environmental circumstance, an expression of a gene combined to the down stream of the promoter is arbitrarily controlled to happen only when it is needed.

FIGS. 1B–FIG. 1E show the above. FIG. 1B shows a status in which gene 102 is combined with a promoter 103 responsive to an environmental circumstance. FIG. 1C shows a status in which gene 104 is combined with a promoter 105 specified to a tissue of plant. FIG. 1D shows a status in which gene 106 is combined with a promoter 107 specified to a growing period. Further, FIG. 1E shows a status in which genes 102, 104 and 106 is combined sequentially then introduced into a plant, and in which the above promoters specified to each condition are sequentially introduced at the upper stream of the combined genes.

According to the above, the present invention provides a promoter of the P5CS gene which controls a gene expression responsive to an environmental circumstance, namely, turning on a gene expression when an environmental circumstance becomes wrong and turning off the gene expression when the environmental circumstance becomes right. The promoter of the P5CS gene of the present invention controls to induce or suppress the expression of a useful gene, such as a gene resisting an environmental stress, connected to down stream of the promoter. Therefore, when there is a change of an earth environment, it is possible to control whether a plant resists against such an environmental stress. Further, if the promoter of the P5CS gene is combined with a gene which dyes a tissue of the plant, it is possible to monitor a status change of the tissue corresponding to environmental circumstance, i.e., a sensor plant corresponding to an environmental stress.

It is known that many plants accumulate proline, a kind of amino acid, in cells when they are subject to water stress, in which the plant has difficulty getting water, such as through drought or salinity stress. The proline is synthesized from two enzymes of P5CS "$\Delta^1$-pyrroline-5-carboxylate synthetase" $\Delta^1$- and P5CR "-pyrroline-5-carboxylate reductase". It is known that P5CS is a rate-limiting step of proline biosynthesis under water stress. Further, it is known that the P5CS gene is rapidly induced to express under water stress, such as dry stress or osmotic stress, and given an abscisic acid (ABA), and the P5CS gene is rapidly suppressed to express in the absence of the stress and the abscisic acid (ABA).

As such, the inventor came up with an idea that the promoter of the P5CS gene may induce an expression of a gene corresponding to environmental circumstance. Namely, the expression of a gene is controlled by the P5CS promoter via giving to a plant or removing from the plant an environmental stress. Cloning and sequence analysis of genomic DNA including the promoter region of the P5CS gene from *Arabidopsis thaliana* are executed.

The promoter region of the P5CS gene is taken out and combined with a β-glucuronidase gene so that the chimeric gene is introduced into a plant. An expression of the β-glucuronidase gene of a plant introduced in the chimeric gene is induced under dehydration stress or osmotic stress via abscisic acid (ABA) biosynthesis.

The promoter of the P5CS gene can control an expression of a gene under water stress. Namely, the present invention provides a DNA including the promoter of the P5CS gene. Further, the present invention provides a vector for a plant including the above DNA.

BRIEF DESCRIPTION OF THE DRAWINGS

FIG. 2 shows an upper part of a Nucleotide sequence of genomic DNA described in SEQ ID NO. 1 of the sequence listing, which is renumbered based on function thereof.

FIG. 3 shows a lower part of a Nucleotide sequence of genomic DNA described in SEQ ID No. 1 of the sequence listing, which is renumbered based on function thereof.

FIGS. 6A and 6B show photographs showing the result of expression of a gene with the promoter of the present invention.

DESCRIPTION OF THE PREFERRED EMBODIMENT

As described above, the DNA of the present invention includes the P5CS promoter. Although the origin of the P5CS promoter is not limited specially, the embodiment shown in SEQ ID NO. 1 of the sequence listing discloses a P5CS gene cloned from *Arabidopsis thaliana* and at least one promoter thereof.

SEQ ID NO. 1 of the sequence listing shows a nucleotide sequence of the genomic DNA of the promoter region of P5CS cloned from *Arabidopsis thaliana* and the first exon thereof.

For the convenience of explanation, the nucleotide sequence of genomic DNA shown in SEQ ID NO.I of the sequence listing is renumbered based on function thereof as shown in FIG. 2 and FIG. 3. An upper stream part and a lower stream part of the nucleotide sequence of genomic DNA shown in SEQ ID NO. 1 are separately shown in FIG. 2 and FIG. 3 due to the width of a paper. In the nucleotide sequence of FIG. 3, a base pair starts at a position marked by an arrow and a character +1, and base pairs atg starting from +124 which is a sequence coding of a first amino acid of P5CS protein. TATA box necessitated to transcript of a gene is recognized at −30 of the sequence (underlined). ABRE of cis-acting motif being responsible to ABA, which is a kind of plant hormone, exists at −86 of the sequence (underlined). Further, it is recognized that a sequence, to which transcription factor (MYC and MYB) are expected to be combined, and CCAAT of cis-acting motif, exists. In the present embodiment, a DNA which exists from −0164 to +70 in the nucleotide sequence of genomic DNA shown in SEQ ID NO. 1 is combined with a vectorso that an expression of a foreign gene existing at the down stream of the DNA is accomplished.

Figure 1A:
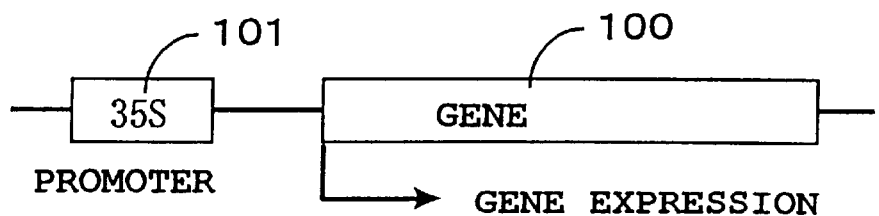
FIG. 1A–FIG. 1E respectively show the interaction between a vector for a plant and an expression of gene.
Figure 1B:
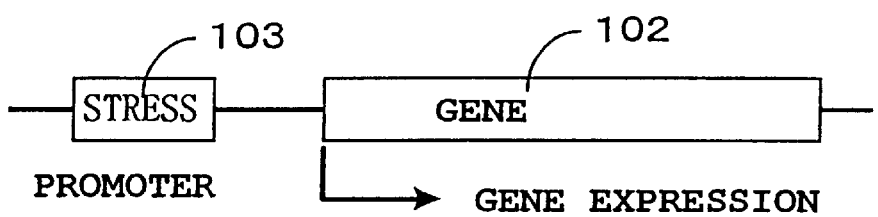
Figure 1C:
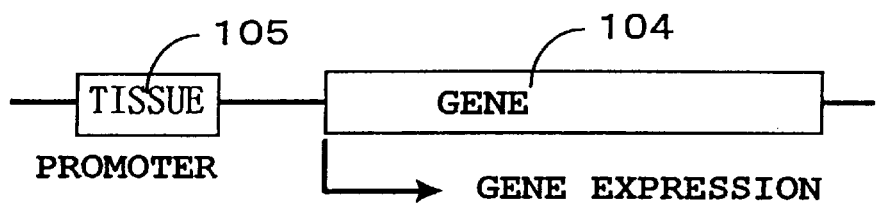
Figure 1D:
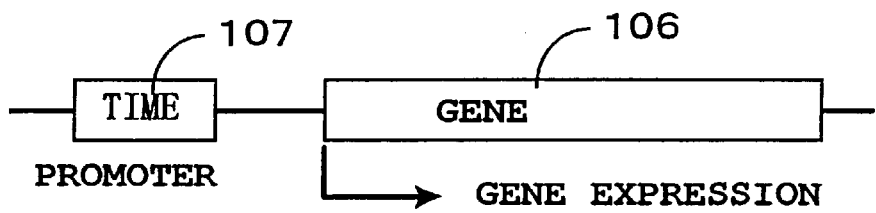
Figure 1E:
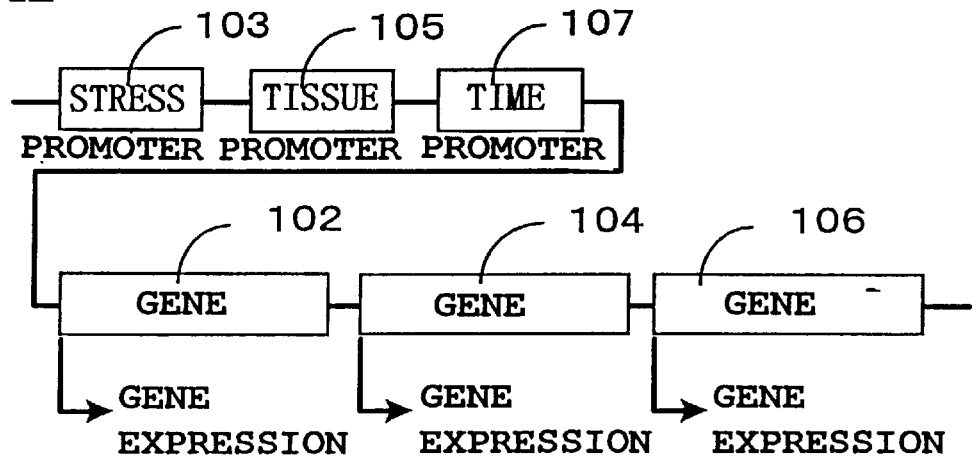
Figure 4:
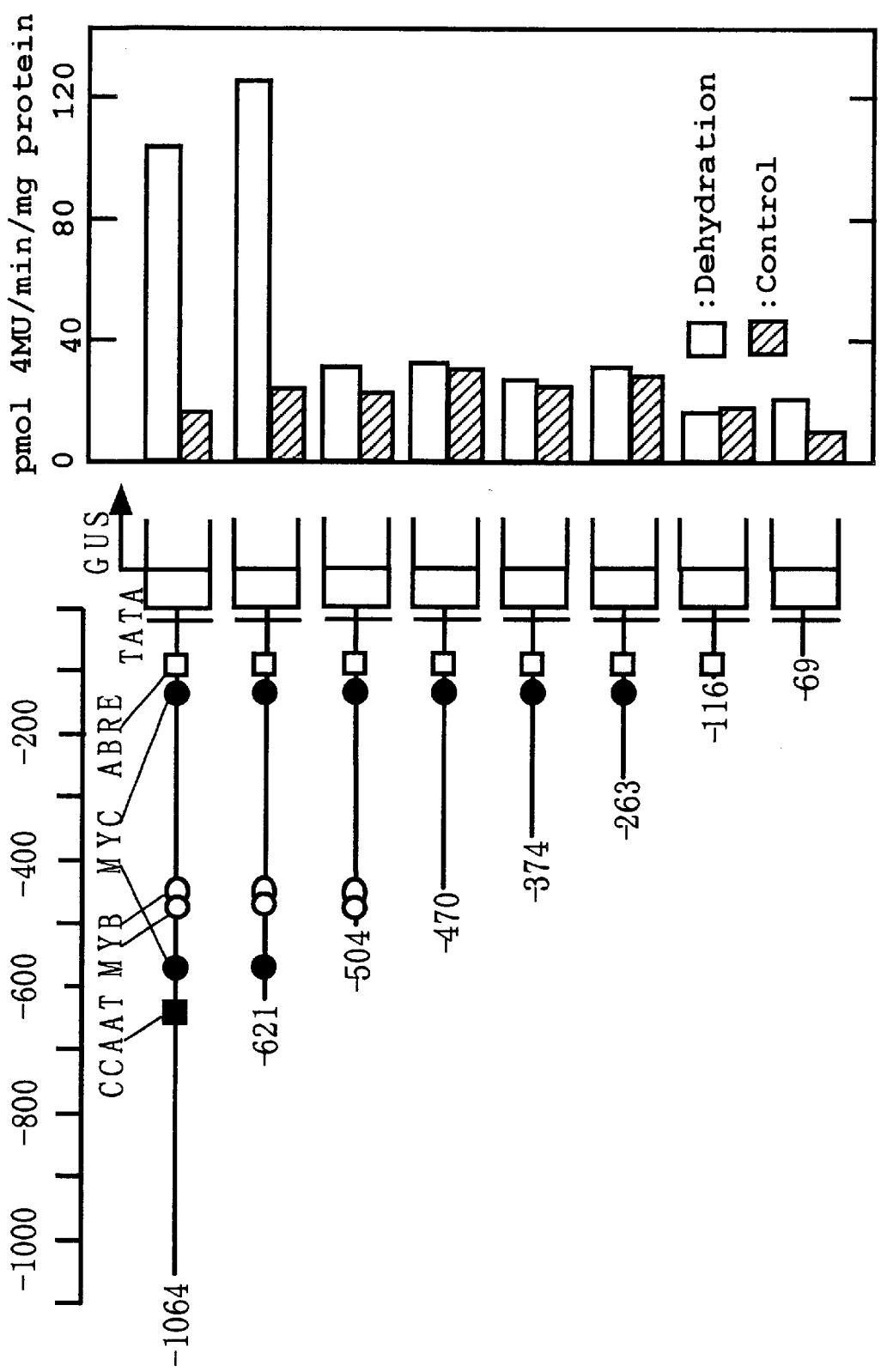
FIG. 4 shows an analysis of the responsiveness to dehydration of the P5CS promoter and its deletion series in transgenic *Arabidopsis thaliana* plants, wherein DNA of the present embodiment is deleted from upper stream (5' site) and is combined with a vector with a foreign gene in down stream.

FIG. 4 shows an analysis of the responsiveness to dehydration of the P5CS promoter and its deletion series in transgenic *Arabidopsis thaliana* plants. The DNA of the present embodiment is deleted from upper stream (5' site) and is combined with a vector with a foreign gene in down stream. In FIG. 4, some DNAs deleted from upper stream (5' site) are shown at the left side and expressions of the foreign genes in down stream are shown at the right side. Where the numeral shown at left side means number of base pairs based on a base pair of +1 shown in sequence listing of FIGS. 2 and 3. The positions of a cis-acting motif (CCAAT), a transcription factor (MYC and MYB) a cis-acting motif being responsible to ABA (ABRE), and TATA box are shown by a black rectangular box, a black and a white circular, a white rectangular box and a vertical short line, respectively. The expression of a gene under dehydration is shown by a white bar graph and the expression of a gene under control is shown by a bar graph with stripes.

The first stage shows the expression of a foreign gene of the present embodiment.

The second stage shows the expression of a foreign gene of the present embodiment in which DNA is deleted from upper stream (5' site) by No. −621.

The third stage from the top shows the expression of a foreign gene of the present embodiment in which DNA is deleted from upper stream (5' site) by No.−504.

The fourth stage (lowest) shows the expressions of a foreign gene of the present embodiment in which DNA are deleted from upper stream (5' site) by the shown number in the figure.

From comparison between the expression of the foreign gene of the second stage and the expression of the foreign gene of the third stage, it appears that the expression by the sequence deleted by No. −621 of base pairs is observed but the expression by the sequence deleted by No. −504 of base pairs is not observed. It is recognized from this that activity of the promoter exists in 117 base pairs between −621 and −504.

Therefore, it is clear that the promoter of the present invention is included in DNA described in SEQ ID NO. 1 of the sequence listing.

The present invention provides a vector for a plant cell including the DNA as discussed. The vector of the present invention is gotten from above described DNA in (SEQ ID NO. 1 of the sequence listing ). The vector is combined into a plasmide in which a copy starting point for copying autonomously in a host cell and a suitable marker, preferably drug resistance, for example.

Vectors pBI101, pBI121 or pB1221 (made by Clonetech company) known for plant are used as a plasmide of the above. The vector of the present invention is made from that DNA described in SEQ ID NO. 1 of the sequence listing then combined into at the cloning position of the known vectors. In the following embodiment, the vector of the present invention is constructed by the DNA sequence of base pairs from number −1064 to number +70 shown in FIGS. 2 and 3, then combined with HindIII-BamHI digestion of the above pBI101.

In the vector of the present invention, a structural gene (coding a desired protein) is combined with a down stream of the DNA described in SEQ ID NO. 1 of the sequence listing. In the following embodiment of the present invention, vector-P5CS-pro/GUS, in which the β-glucuronidase is combined as a structural gene, is obtained.

The DNA and the vector of the present invention, in the case of *Arabidopsis thaliana*, is arranged as follows. But the present invention is not limited to the described method.

First, a genomic DNA library of *A. thaliana*, Columbia ecotype (Clontech, Palo Alto, Calif., USA) is screened by using the full-length P5CS1 cDNA of *A. thaliana* as a DNA probe for hybridization. Then a P5CS1 gene promoter from *A. thaliana*, Columbia is isolated.

An experiment to assay the activity of a promoter is executed as follows. A part of the DNA described in SEQ ID NO. 1 of the sequence listing, in which a promoter's activity may be included, is combined with the upper stream (5' site) of the β-glucuronide (GUS) gene. GUS does not naturally exist in a plant and is detected by a quantitative analysis of a strong fluorescence generated by a reactant of 4MU which is a material of that 4-methylumbelliferone (4MU) and reacts with a 4-MUG as a substrate combined Glucuronic acid (Jefferson et al. EMBO J. vol.6, no.13:3901–3907

(1989)). Recombinant plasmid recombined with a promoter of P5CS gene, and a GUS gene is induced to a flower immediately after flowering by the vacuum infiltration method through an Agrobacterium tumefaciens (Bechtold et al. CR Acad. Sci. Ser. III Sci. Vie. 316:1194–1199 (1993)). The plant induced by the plasmid is grown by heading and harvested. The harvested seeds are sown on a germination medium in which a suitable marker (including drug resistance for selection of vector) is contained and an individual plant is selected by whether or not the seed can germinate.

A selection of the individual plant is executed as follows. If the DNA including the promoter of the present invention is combined with pBI101 including GUS gene, the selection is executed based on a plant's resistance against kanamycin. Since pBI101 includes a NTP11 gene, the plant has a resistance against kanamycin when the enzyme is produced in the plant. Therefore the plant, which can be grown or germinated under existence of kanamycin, probably has a chimeric gene of a promoter of the P5CS gene and the GUS gene. Thus, the GUS gene expresses in the whole plant under dehydration stress or high salt stress.

The promoter of the P5CS gene of the present invention controls expression of the gene so that expression of the gene is only induced under circumstance stress, especially water stress, from outside. Since the gene expresses strongly in young plant organs which are weak against circumstance stress, it is suggested that a plant resistant against circumstance stresses effectively may be provided by combining the promoter and a foreign gene for protecting the young plant organs from circumstance stresses.

The present invention is further described by an embodiment below but it is not limited to the embodiment. The operations of the embodiment are based on the method described in "Molecular Cloning Cold Spring Harbor Laboratory Press (1989)" by Sambrook et al.

(An Experiment)

First, a genomic DNA library of *A. thaliana,* Columbia ecotype (Clontech, Palo Alto, Calif., USA) is screened by a plaque hybridization using the full-length P5CS1 cDNA (Plant J. 7:751–760 (1995), Yoshiba et al. ) of *A. thaliana* as a probe. Seven positive genomic DNAs re purified. These clones are made into small DNA fragments by restriction enzyme digestion of Eco RIARind III.

These DNA fragments are subcloned into the pSK vectors and sequences thereof by cycle sequencing methods with a DNA sequencer (model 373A; Applied Biosystems, Calif., USA). Then a 3492 bp fragment having first exon at 3' site of P5CS gene is gotten. The nucleotide sequence of genomic DNA shown in SEQ ID NO. 1 of the sequence listing is the sequence of promoter region of the P5CS gene including the first exon.

Figure 5:
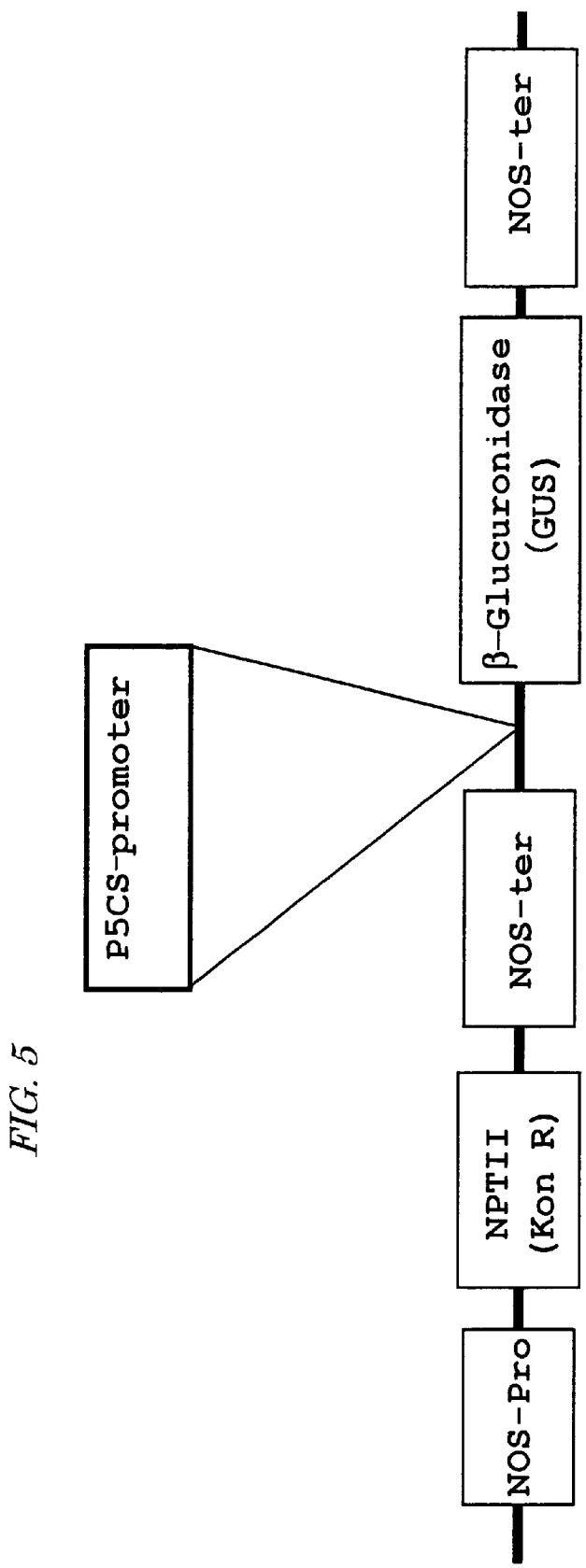
FIG. 5 shows a gene map of plasmide P5CS-Pro/GUS constructed by the β-glucuronidase (GUS) gene included in vector pBI101 for a plant and the P5CS promoter described in SEQ ID NO. 1 of the sequence listing combined at the upper part of the GUS.

Next, in order to assay the activity of the promoter of the P5CS gene, the promoter region of the P5CS gene is amplified by a PCR method and connected to a GUS gene. Namely, the DNA fragment of sequence of 1134 base pairs from number −1064 to number +70 shown in FIGS. 2 and 3 is amplified by a PCR method, wherein a primer having a restriction enzyme recognition site for the Hindlll is combined with 5' site thereof, and a primer having a restriction enzyme recognition site for the BamHI is combined with 3' site thereof. Then the amplified DNA fragments and plasmid pBI101 are restricted by restriction enzymes at the site of the Hindlll and the BamHI, respectively. A plasmid P5CS-Pro/GUS is constructed by a DNA Fragment P5CS-Pro (including a promoter of P5CS gene) which is connected to the above restricted site. The gene map of plasmide P5CS-Pro/GUS is shown in FIG. 5.

Further, in order to specify an activity cite of the promoter of the present invention, deletion series in transgenic *Arabidopsis thaliana* plants are made, wherein DNA of the present embodiment is deleted from upper stream (5' site) then combined with a vector with a GUS gene in down stream. The GUS activity is determined using the transgenic plants.

FIG. 4 shows, as described above, the GUS activity (left side of FIG. 4) according to the length of the DNA fragments including the introduced promoter part (right side of FIG. 4). In order to analyze the GUS gene's activity, transgenic *Arabidopsis thaliana* plants are grown under germfree and extracted from a medium without damaging the root before running to seed. The extracted transgenic plants are put on filter papers under dehydration and analyzed by a method of Jefferson et at. (EMBO J. vol. 6, no. 13; 3901–3907 (1989)). The analysis is executed by measuring fluorescence strength of 4MU which is a product by digestion of 4MUG with enzyme of a product of the P5CS gene.

According to the result shown in FIG. 4, it is suggested that the activation part of the promoter of the present invention exists on the base pairs between the bp number −621 and −504.

(Example of Results of Experiment)

FIGS. 6A and 6B show photographs showing the result of the expression of the GUS gene with the promoter of the present invention. This example shows the experimental result of the transgenic *Arabidopsis thaliana* plants in which the plasmide P5CS-Pro/GUS to which the promoter including the DNA fragments of sequence of 1134 base pairs from number −1064 to number, +70 is combined, is introduced. FIG. 6A shows the result of plant dehydration and FIG. 6B shows the result of plants under dehydration during 24 hours. Both are detected by the method of Jefferson et al. (EMBO J. vol.6, no. 13: 3901–3907 (1989)) in which the GUS gene expression part is dyed in blue by 4-methyl umbelliferyl glucuronide (X-Gluc) and detected. Since FIGS. 6A and 6B are not colored, they show only contrast of black and white. But the plant under dehydration shown in FIG. 6B is black comparing the plant not under dehydration shown in FIG. 6B. This means that the plant expresses the GUS gene under dehydration. Further, it is remarkable that the expression is strong at young leaves or roots of plants. Namely, since the expression is stronger at younger organs of plants, useful plants are effectively protected from a circumstance stress if a stress resistant gene is combined with a promoter. Further, it is possible to produce plants which will grow under sever circumstances.

Similarly, GUS gene expressions are observed under high salt treatment in which plants are dipped in a solution of 250 mM NaCl, or under ABA treatment, in which plants are dipped in a solution of 100 $\mu$M ABA similar to under dehydration.

Further, it is possible to monitor the status if a gene which is capable of emitting light is combined with down stream of the promoter of the present invention then introduced in plants.

It is well known in the field of the present invention that even though if a small number of base pairs are replaced, missed or added to a DNA fragment having a predetermined function, the changed DNA fragment operates the predetermined function in the same way as the original DNA fragment. Therefore, in the present invention, if a small number of basc pairs are replaced, missed or added to the DNA fragment shown in SEQ ID NO. 1 of the sequence listing, the changed DNA fragment operates as the promoter in the same way as the promoter described above.

According to the present invention, new DNA fragments and new vectors for plants having the new DNA fragment including a promoter which controls gene expression according to water stress (circumstance stress) are provided. The plants into which the new vector provided by the present invention is introduced express gene under water stress. The expression of gene is observed in the whole plant, especially in younger organs, such as root caps, lateral roots or flowers. This means that the plants are protected from circumstance stresses and can grow under circumstance stresses.

What is claimed is:

1. A DNA fragnent comprising a promoter from $\Delta^1$-pyrroline5-carboxylate synthetase 1 gene constructed into a vector for improving a plant's resistance against dehydration stress, wherein the DNA fragment comprises the DNA from nucleotide 640 to nucleotide 1330 or from nucleotide 197 to nucleotide 1330 in SEQ ID No. 1 of the sequence listing.

2. A DNA fragment comprising a promoter from $\Delta^1$-pyrroline-5-carboxylate synthetase 1 gene which is originated from *Arabidopsis thaliana* constructed into a vector for improving a plant's resistance against dehydration stress, wherein the DNA fragment comprises the DNA from nucleotide 640 to nucleotide 1330 or from nucleotide 197 to nucleotide 1330 SEQ ID No. 1 of the sequence listing.

3. A vector DNA fragment which has a dehydration stress inducible promoter function in an organ of a plant and is originated from $\Delta^1$-pyrroline-5-carboxylate synthetase 1 gene, wherein the DNA fragment comprises the DNA from nucleotide 640 to nucleotide 1330 or from nucleotide 197 to nucleotide 1330 in SEQ ID No. 1 of the sequence listing.

4. A vector DNA fragment which has a dehydration stress inducible promoter function in an organ of a plant and is originated from $\Delta^1$-pyrroline-5-carboxylate synthetase 1 gene, wherein the $\Delta^1$-pyrroline-5-carboxylate synthetase 1 gene is originated from *Arabidopsis thaliana*, and the DNA fragment comprises the DNA from nucleotide 640 to nucleotide 1330 or from nucleotide 197 to nucleotide 1330 in SEQ ID No. 1 of the sequence listing.

5. A plant sensing dehydration condition and having a gene capable of dyeing a tissue of the plant in response to the dehydration condition, wherein said plant comprises the DNA fragment which has a dehydration stress inducible promoter function in an organ of a plant and is originated from $\Delta^1$-pyrroline-5-carboxylate synthetase 1 gene wherein the DNA fragment comprises the DNA from nucleotide 640 to nucleotide 1330 or from nucleotide 197 to nucleotide 1330 in SEQ ID No. 1 of the sequence listing.

6. A plant sensing dehydration condition and having a gene capable of dyeing a tissue of the plant in response to the dehydration condition, wherein said plant comprises the DNA fragment which has a dehydration stress inducible promoter function in an organ of a plant and is originated from $\Delta^1$-pyrroline-5-carboxylate synthetase 1 gene, wherein the $\Delta^1$-pyrroline-5-carboxylate synthetase 1 gene is onginated from *Arabidopsis thaliana,* and the DNA fragment comprises the DNA from nucleotide 640 to nucleotide 1330 or from nucleotide 197 to nucleotide 1330 in SEQ ID No. 1 of the sequence listing.

7. A method for constructing a vector comprising the steps of:

providing a DNA fragment having a dehydration stress inducible promoter function in an organ of a plant and being originated from $\Delta^1$-pyrroline-5-carboxylate synthetase 1 gene; and constructing the DNA fragment into a vector, wherein the DNA fragment comprises the DNA from nucleotide 640 to nucleotide 1330 or from nucleotide 197 to nucleotide 1330 in SEQ ID No. 1 of the sequence listing.

8. A method according to claim 7, wherein the $\Delta^1$-pyrroline-5-carboxylate synthetase 1 gene is originated from *Arabidopsis thaliana*.

* * * * *